United States Patent [19]
Bombardelli et al.

[11] Patent Number: 5,700,468
[45] Date of Patent: Dec. 23, 1997

[54] **EXTRACTS OF *GINKGO BILOBA* AND THEIR METHODS OF PREPARATION**

[75] Inventors: Ezio Bombardelli; Giuseppe Mustich; Marco Bertani, all of Milan, Italy

[73] Assignee: Indena SpA, Milan, Italy

[21] Appl. No.: 615,536

[22] Filed: Mar. 12, 1996

Related U.S. Application Data

[63] Continuation of Ser. No. 445,916, May 22, 1995, Pat. No. 5,637,302, which is a continuation of Ser. No. 316,411, Jul. 26, 1994, abandoned, which is a continuation of Ser. No. 263,026, Jun. 20, 1994, abandoned, which is a continuation of Ser. No. 151,267, Nov. 12, 1993, abandoned, which is a continuation-in-part of Ser. No. 7,006, Jan. 21, 1993, abandoned, which is a continuation of Ser. No. 882,372, May 6, 1992, abandoned, which is a continuation of Ser. No. 769,106, Sep. 30, 1991, abandoned, which is a continuation of Ser. No. 408,235, Sep. 18, 1989, abandoned.

[30] Foreign Application Priority Data

Sep. 20, 1988 [GB] United Kingdom ................. 8822004

[51] Int. Cl.$^6$ ................. A61K 47/16; A61K 47/00; C07K 14/00

[52] U.S. Cl. ................. 424/195.1; 514/12
[58] Field of Search ................. 424/195.1; 514/12

[56] References Cited

U.S. PATENT DOCUMENTS

| | | | |
|---|---|---|---|
| 4,571,407 | 2/1986 | Chatterjee et al. | 514/264 |
| 4,886,904 | 12/1989 | Tanaka et al. | 560/249 |
| 5,043,323 | 8/1991 | Bombardelli et al. | 514/25 |

*Primary Examiner*—Cecilia J. Tsang
*Assistant Examiner*—P. Lynn Touzeau
*Attorney, Agent, or Firm*—Kirschstein, Ottinger, Israel & Schiffmiller, P.C.

[57] ABSTRACT

A process is provided for producing a purified extract from *Ginkgo biloba* leaves by solvent extraction with selected solvents. In the process, a crude or partially purified extract is subjected to solvent extraction with a solvent comprising toluene and n-butanol. Pharmaceutical compositions comprising dimeric flavones and/or polyphenols are also described.

2 Claims, No Drawings

1

EXTRACTS OF *GINKGO BILOBA* AND THEIR METHODS OF PREPARATION

CROSS-REFERENCE TO RELATED APPLICATIONS

This application is a continuation of Ser. No. 08/445,916 filed May 22, 1995, now U.S. Pat. No. 5,637,302, which is a continuation of Ser. No. 08/316,411, filed Jul. 26, 1994, abandoned which is a continuation of Ser. No. 263,026 filed Jun. 20, 1994, abandoned which is a continuation of Ser. No. 08/151,267, filed Nov. 12, 1993, abandoned, which is a continuation-in-part of Ser. No. 08/007,006, filed Jan. 21, 1993, abandoned, which is a continuation of Ser. No. 07/882,372, filed May 6, 1992, abandoned, which is a continuation of Ser. No. 07/769,106, filed Sep. 30, 1991, abandoned, which is a continuation of Ser. No. 07/408,235, filed Sep. 18, 1989, abandoned.

The present invention relates to a process for producing novel extracts of *Ginkgo biloba* leaves.

The invention particularly relates to a procedure which can lead to extracts having chemical compositions and biological activities which correspond closely to those described in the literature but from which undesired components have been substantially eliminated.

The invention further provides new extracts which find application in both the therapeutic and the cosmetic field.

Methods of preparing active extracts of *Ginkgo biloba* leaves have been described in DE 1767098 and DE 2117429 (Dr. Willmar Schwabe) and in JP 1167714. For some extracts prepared in accordance with the process described in these patents, activities are claimed which cannot readily be ascribed to a single class of compounds. This is in contrast to what can be inferred from the simple chemical characterisation of the extracts quoted in these patents.

In fact, in these patents, reference is made in a very superficial manner to the classes of active principles responsible for the multiplicity of actions which are claimed. For example, DE 2117429 describes an improvement of the procedure of DE 1767098, by which purification is effected to permit injectability of the resulting preparation. According to this process, catechic polymeric derivatives of a tannic nature normally not compatible with the blood are apparently eliminated leaving the remaining portion unchanged.

Subsequent search has made it clear that some constituents present in the extracts obtained by the processes initially described have special activities. For example, in BE 902874 and ZA 8848369 there are described activities relating to individual components, such as the ginkgolides and bilobalide, which were normally present in the known extracts previously employed in therapy (see e.g. the work of S. S. Chatteyee, *Arztezeitschrift für Naturheilverfahren* 22, 595–604, 1981).

The known extracts prepared from *Ginkgo biloba*, which have been used in medicine since 1965 for the therapy of cerebral disturbances and pathologies correlated with changes in the peripheral circulation, contain (at least as far as it is possible to determine with the analytical methods currently available) flavone glycosides as principal components. Among these, the most important have proved to be 5,7,3,4-tetrahydroxyflavone-3D-α-rhamnopyranosyl-4-D-β-0-(6'''-transcoumaroyl)-glucopyranoside and 5,7,3,4',5'pentahydroxyflavan-3D-α-rhamnopyranosyl-4-β-0-(6'''coumaroyl) glucopyranoside.

As is apparent from the work described by Chatteyee (supra), ginkgolides and bilobalide are also present in the known extracts.

Also present in these extracts are other flavonoids such as quercetin-3-rhamnoside and kaempferol-3-rhamnoside, luteolin-7-glucoside and derivatives of isorhamnetin and of quercetin, such as rutin and quercetin-3-glucoside.

Known extracts also contain proanthocyanidines and undesirable lipophilic substances such as alkylphenols. All of these substances (including the undesired ones) are generally present in hitherto known extracts, including ones which have been available since the time when derivatives of the plant were introduced into the European market for therapeutic use.

Analyses carried out by us on medicinal specialities on the market in various European countries have supplied data which are in perfect accord both with the work published by Chatteyee (supra) and with the more recent work reported in *La Presse Médicale* 15, 1455–7, 1986, and in "Flavonoids and Bioflavonoids" Eds. L. Farkas, Elsevier 1986, page 351.

Among the flavones, it has been verified that the principal components are in effect the coumaroyl derivatives respectively of 3-rhamnoglucoside of quercetin and of caempferol.

This last compound is today considered to be the active constituent (or the most important active constituent) of the flavonoidic fraction, as reported in the work of Braquet et al. ("Plant Flavonoids in Biology and Medicine" Strasbourg 1987), while of lesser importance in terms of biological activity are the other constituents having a flavonic skeleton.

As a result of analyses carried out by HPLC and by gas chromatography/mass spectrometry, it has become apparent that in the extracts used up to today in therapy, significant amounts of ginkgolides and bilobalide are present, as well as substances which are minor components, but which are important for the purposes of bioavailability, such as p-hydroxybenzoic acid, kyurenic acid and hydroxykynurenic acid, etc (*La Presse Médicale*, supra).

The polyphenolic portion of the known extracts have now been characterized by us more specifically using what we term the "procyanidolic index". This index supplies an indirect value of the content of catechic derivatives (after acid hydrolysis), i.e. the quantity of anthocyanidines formed by acid catalysed decomposition of oligomeric condensed polyphenols.

This characterisation indicates the type of oligomer present on the basis of the catechic and anthocyanidinic monomers which are liberated. In these analyses, in fact, catechin, gallocatechin, cyanidin and delphinidin have been determined, and provide a pointer to the catechic nature of the oligomeric polyphenolic fraction.

Following these studies, and this constitutes one aspect of this invention, a new industrial process has been developed for the preparation of *Ginkgo biloba* extracts. The new procedure allows the production of extracts which can be identical (so far as can be reasonably established for a plant derivative) to the products employed today in therapy in that they contain the various classes of known substances in *Ginkgo biloba*, but enables drawbacks if known extraction processed to be avoided. In particular the novel procedure enables undesired lipophilic substances, especially alkylphenols, to be eliminated.

Also two novel extracts have been perfected. One is constituted by a dimeric flavonoids fraction, and provides a new active product useful in the therapy of disturbances of the cerebral and peripheral circulation, in disorders due to platelet aggregation and in those morbid manifestations in which antiphosphodiesterasic activity is useful. The second comprises an extract constituted by the total polyphenolic fraction and which is useful, above all, for the treatment of superficial vasculopathies and for topical treatments of changes in the microcirculation.

This second extract can be produced in a form which contains all the free flavonoidic substances and their glucosidated derivatives present in *Ginkgo biloba*, as well as the proanthocyanidinic oligomeric fraction characteristic of the plant. However it does not contain lipophilic substances which are poorly soluble in water, e.g. alkylphenols.

According to the scientific and patent literature, the processes hereinbefore described involve extraction with pure aliphatic alcohols or ketones or with aqueous mixtures of such alcohols or ketones which are miscible with water, employing predetermined amounts of solvents. The following stages involved direct counter-extraction of the extracts with halogenated hydrocarbons to remove the lipophilic substances. Finally, after saturating the aqueous solution with ammonium sulphate with or without treatment of the solution with lead (or other heavy metals) salts or with polyamides (when it was intended to reduce the tanninic part) the active principles were extracted with methyl ethyl ketone. The ketonic organic phase was dehydrated, concentrated to a low volume and, after treatment with ethanol, evaporated to dryness.

These methods had the fundamental disadvantage of using large volumes of different solvents which are miscible with one another, very large quantities of salts for facilitating the extraction and the separation of the phases and, in some situations, polluting lead salts. Also the known procedures were incapable of efficiently removing lipophilic unwanted materials without the simultaneous loss of desired components.

In other words, the known procedures fail to produce extracts which satisfied the dual criteria of (1) ensuring that desired ginkgo flavoneglucosides, proanthocyanidines, ginkgolides and bilobalide were retained and (2) that lipophilic substances were eliminated.

We have now developed a procedure for obtaining purified extracts of *Ginkgo biloba* which avoids or reduces drawbacks of prior art processes. Furthermore, the process of the invention enables extracts to be obtained which contain the active components of the plant in proportions which can be selected, if desired, to correspond to those present in the plant itself or in known extracts, but from which lipophilic substances have been eliminated.

According to one aspect of the invention there is provided a composition comprising compounds extracted from leaves of *Ginkgo biloba* and consisting essentially of ginkgo flavone glucosides, proanthocyanidines, ginkgolides and bilobalide and wherein inactive lipophilic substances which can be extracted by n-hexane, n-heptane or a solvent comprising a major proportion of toluene and a minor proportion of n-butanol (especially one in which the volume ratio of toluene:butanol is from 6:1 to 12:1) are substantially absent.

The compositions of the invention preferably consist essentially of the following components:

| | |
|---|---|
| ginkgo flavone glucosides | 22–26 wt % |
| proanthocyanidines | <10 wt % |
| ginkgolides | 2.5–4.5 wt % |
| bilobalide | 2.5–4.5 wt % |
| lipophilic substances | substantially absent |

According to a further aspect of the present invention, there is provided a process for producing a purified extract comprising a plurality of the active components of *Ginkgo biloba* leaves especially ginkgo flavone glucosides, proanthocyanidines, ginkgolides and bilobalide, which comprises subjecting a crude or partially purified extract of *Ginkgo biloba* leaves to a plurality of solvent extraction procedures, characterized in that at least one of said solvent extraction procedures employs a solvent comprising a toluene and preferably n-butanol.

The use of a solvent comprising toluene and butanol offers a number of significant advantages in the production of *Ginkgo biloba* extracts, including the following:

(1) it has been found that such solvents are particularly effective in extracting a large number of the desired active components, (2) the solvents, particularly toluene and butanol, are miscible and it is possible to produce a range of solvents having differing affinities of substances of different polarities. Thus relatively lipophilic (i.e. less polar or hydrophobic) substances may be extracted using solvents containing a relatively high proportion of toluene, i.e. one comprising toluene and n-butanol in a volume ratio of toluene:butanol from 6:1 to 12:1. Conversely hydrophilic (i.e. more polar) substances may be extracted using solvents containing a relatively high proportion of butanol, i.e. one wherein the volume ratio of toluene:butanol is in the range of 1:2 to 1:5.

(3) extraction procedures may be devised in which the number of different organic solvents used is low (e.g. two or three). This gives rise to significant cost savings and increases the ease with which valuable solvents may be recycled.

(4) the use of heavy metal salts may be avoided.

(5) the selected solvents present less toxicity hazards than chlorinated hydrocarbon solvents used in defatting steps of prior art processes.

(6) lipophilic substances can be eliminated while ensuring that ginkgo flavone glucosides, proanthocyanidines, ginkgolides and bilobalide are retained.

By way of example of advantages (2) and (5), in accordance with one preferred method of operation according to the invention, a solvent comprising a major proportion of toluene and a minor proportion of n-butanol is used to extract fatty materials from an extract of *Ginkgo biloba* leaves. Preferably the volume ratio of toluene: butanol is greater than 6:1, e.g. from 6:1 to 12:1, most preferably about 9:1.

By way of example of advantages (1) and (2), in accordance with another preferred method of operation according to the invention, a solvent comprising a minor proportion of toluene and a major proportion of n-butanol is used to extract desired active components from an extract of *Ginkgo biloba* leaves. Preferably the volume ratio of toluene:butanol is less than 1:2 and most preferably is about 1:4.

The crude or partially purified extract used in the process of the invention may be obtained by any convenient means.

Preferably according to the process of the present invention, a starting material formed from finely ground, still green, machine-dried leaves, is extracted to exhaustion with an aqueous solvent comprising a mixture of acetone and water or a mixture of methanol and/or ethanol and water. The concentrations of the organic component expressed as a percentage of the total volume of solvent employed preferably comprises between 45 and 99%. The extraction temperature is preferably between 15° and 70° C.

These partially aqueous extracts can then be extracted directly with n-hexane or with n-heptane or, in accordance with a preferred embodiment of the invention, with a toluene/butanol mixture to remove inactive lipophilic substances such as chlorophyll, ginkgolic acids, polyphenols, aliphatic alcohols, free and esterified sterols, etc. The hexane or the toluene/butanol mixture used as solvents do not extract, for example, ginkgolides and bilobalides (which are also lipophilic substances) but whose presence is desired in the final product.

Alternatively, the water-acetone, water-methanol or water-ethanol extracts may be concentrated to a water solution having a volume equal to double the weight of the drug. In this case, the concentrate is diluted with alcohol (ethanol or methanol) or with acetone so as to re-establish an appropriate ratio of water/organic solvent prior to extraction of lipophilic substances.

The defatted solution may then be concentrated to a volume equal to the weight of the drug and then the concentrate may be kept in a refrigerator for 24 hours at a temperature of about 2° C. and then centrifuged. The semi-crystalline precipitate which is separated by centrifuging comprises a mixture of dimeric flavonoids (sciadopitisin, ginkgonetin, isoginkgonetin, bilobetin, amentoflavone) which can be employed as such or after recrystallization for formulations for therapeutic or cosmetic use.

The aqueous phase, after centrifuging as stated above, may be extracted in countercurrent with a toluene/butanol mixture in which the volume ratio of toluene:butanol may vary from 1:2 to 1:4.

These mixtures readily extract substantially all the active principles present, but extract the condensed polyphenolic substances such as the thins with extreme difficulty, for which reason the solvents may be regarded as being selective. Naturally, these solvent mixtures do not extract free sugars, polysaccharides, common organic and inorganic salts and proteins and their derivatives.

After careful counterwashing with water, the toluene-butanol phase may be concentrated under vacuum to a paste-like consistency at a temperature not higher than 40° C. and taken up with water or a water-alcohol mixture in order to remove the residual traces of toluene and butanol and dried.

The aqueous solution, which has been defatted and still contains a proportion of the dimeric flavones, can be passed over absorption resins such as Amberlite XAD4, XAD26 or Duolite S-761 these resins readily absorb many substances and have a marked activity for those of a phenolic nature; the same substances can be re-eluted from the resin with pure alcohols or ketones or alcohols or ketones in suitable mixtures with water.

(Duolite S-761 is a hydroxylic phenol-formaldehyde absorption resin with a granulometry of 0.3 to 1.2 mm).

Thus according to a further aspect of the invention there is provided a process for extracting flavanoids from an aqueous extract of *Ginkgo biloba* leaves which comprises contacting the extract with an absorption resin and eluting absorbed flavanoids with an organic solvent.

The absorption resin preferably comprises an aromatic polymer, for example a hydroxyl group containing phenol-formaldehyde resin. The organic solvent is preferably a lower ($C_{1-4}$) alkanol or a water-miscible ketone, either of which may be used in pure form or in admixture with water.

In this case, and this is another aspect of the invention, after absorption and re-elution of the active principles, it is possible to obtain an extract rich in the flavonoid component which lends itself, like the others, to being incorporated in the most common pharmaceutical formulations and, in this specific case, also cosmetic formulations.

The Examples given hereinafter illustrate the more important features of the invention without, however, being limitative.

EXAMPLE I 100 kg of finely ground, dried *Ginkgo biloba* leaves are extracted under agitation 4 times with 400 l of a mixture of acetone and water in a ratio of 60:40 (w/w) at a temperature around 50° C.

The combined water-acetone extracts are extracted continuously in countercurrent with 500 l of n-hexane. In the final stage, the n-hexane solution appears practically colourless. The defatted water-acetone solution is concentrated under vacuum to 200 l at 40° C.; the aqueous concentrate is cooled to 2° C. over night and is then centrifuged. After washing with water and drying, 400 g of a product constituted predominantly by dimeric flavonoids derived from the apigenin are obtained.

The aqueous solution filtered from the dimeric flavonoid fraction is subjected to countercurrent extraction with about 400 l of a mixture of n-butanol and toluene in a volume ratio of 8:2.

The organic phase is washed carefully with demineralized water and is concentrated to a paste under vacuum at a temperature not higher than 40° C. It is taken up with water and dried. The residue is taken up in 50 l of aqueous ethanol at 70%. After filtration, the water-ethanol solution is concentrated to 25 l and the concentrate is atomized.

1.98 kg of yellow-beige extract having the following characteristics are obtained:

| | |
|---|---|
| Content of ginkgoflavoneglucosides | 24% |
| Procyanidolic index | 9% |
| Sulphuric ash | 0.1% |
| Content of ginkgolides | 3.6% |
| Content of bilobalide | 3.1% |

EXAMPLE II 100 kg of finely ground *Ginkgo biloba* leaves are extracted four times with 400 l of an aqueous methanol mixture in a ratio of 1:1 (v/v) at 35° C. The combined extracts are concentrated to 100 l under vacuum and at a temperature not higher than 40° C. The concentrate is diluted with 100 l of methanol and the whole is filtered. The filtered solution is extracted three times with 100 l of an 9:2 toluene-butanol mixture. The organic solution is counterwashed with 50 l of a 1:1 methanol-water mixture. The combined water-methanol phases are concentrated to water and, after filtration, are extracted with 2:8 toluene-n-butanol mixture. After counterwashing with water, the organic phase is dehydrated over sodium sulphate, filtered and concentrated to dryness; the residue is solubilized in 10 volumes of a 2:8 ethanol-water mixture, filtered and atomized. 2.2 kg of product similar to that of Example I are obtained.

EXAMPLE III 100 kg of finely ground *Ginkgo biloba* leaves are extracted four times with 400 l of 60% aqueous methanol (w/w) to exhaustion of active principles.

The combined extracts are concentrated to 350 l at a temperature not higher than 40° C. with addition of acetone and adjustment of the acetone concentration to about 50%.

The so obtained solution is filtered so as to eliminate any lipophyl resinous impurity and extracted two times with 100 l of a 9:1 toluene-butanol mixture.

The hydroacetone phase is concentrated under vacuum until complete elimination of the organic solvent and chromatographed on a column packed with 100 l of Duolite S-761 absorption resin.

After absorption of the solution, continue washing the column with about 300 l of purified water so as to remove salts, sugars and unwanted hydrophilic substances. Elute the column with 90% aqueous methanol and continue washing until a colourless solvent is obtained. The elute is concentrated to dryness of 2.5 kg of product is obtained. The solubility characteristics make it fit for pharmaceutical as well as cosmetic application.

It will be appreciated that the present invention provides a novel process for preparing extracts of Ginkgo biloba with a standardized content of active principles which may be similar to those presently available in therapy for the treatment of vascular disturbances of the peripheral and cerebral circulation. The invention also provides processes for isolating another two extracts, one constituted by the flavonoid fraction represented solely by the dimeric flavones characteristic of this plant and having activity on the peripheral circulation and platelet aggregation, showing a marked antiphosphodiesterasic action, while the second is constituted by the total polyphenolic fraction of the plant which can find use in both the dermatological and the cosmetic field as an anti-inflammatory and vasokinetic agent.

We claim:

1. A composition comprising compounds extracted from leaves of *Ginkgo biloba* and wherein inactive lipophilic substances which can be extracted by n-hexane, n-heptane or a solvent comprising toluene and n-butanol wherein the volume ratio of toluene:butanol is from 6:1 to 12:1 are absent, said composition including the following components:

| | |
|---|---|
| ginkgo flavone glucosides | 24 wt % |
| proanthocyanidines | 9 wt % |
| ginkgolides | 3.6 wt % |
| bilobalide | 3.1 wt % |
| sulphuric ash | 0.1 wt %. |

2. A composition according to claim 1 which is free of alkyl phenols.

* * * * *